(12) United States Patent
Falkenberg et al.

(10) Patent No.: US 6,509,493 B1
(45) Date of Patent: Jan. 21, 2003

(54) METHOD FOR PRODUCING ATROPIC ACID ETHYL ESTER

(75) Inventors: Wolfgang Falkenberg, Westheim (DE); Marco Thyes, Ludwigshafen (DE); Conny Wenz, Gönnheim (DE); Ulrich Schneider, Homburg (DE)

(73) Assignee: Knoll Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/743,894

(22) PCT Filed: Jul. 28, 1999

(86) PCT No.: PCT/EP99/05403

§ 371 (c)(1),
(2), (4) Date: Jan. 17, 2001

(87) PCT Pub. No.: WO00/09469

PCT Pub. Date: Feb. 24, 2000

(30) Foreign Application Priority Data

Aug. 11, 1998 (DE) .......................... 198 36 222

(51) Int. Cl.$^7$ .......................... C07C 69/76; C07C 67/48
(52) U.S. Cl. .......................... 560/104; 560/81
(58) Field of Search .......................... 560/104, 81

(56) References Cited

FOREIGN PATENT DOCUMENTS

| AU | 0003670 | * | 2/1979 |
| EP | A 003 670 | | 8/1979 |

* cited by examiner

Primary Examiner—Johann Richter
Assistant Examiner—Farhad Forohar
(74) Attorney, Agent, or Firm—Keil & Weinkauf

(57) ABSTRACT

A process for preparing ethyl atropate by reacting ethyl phenylacetate with paraformaldehyde in the presence of a base is described and entails employing as ethyl phenylacetate a product which contains not more than 0.03% of the corresponding methyl phenylacetate, and carrying out the reaction in N-methyl-pyrrolidone or N,N-dimethylformamide.

1 Claim, No Drawings

METHOD FOR PRODUCING ATROPIC ACID ETHYL ESTER

This Application is a 371 of PCT/EP99/05403 Filed on Jan. 28, 1999.

The present invention relates to a process for preparing ethyl atropate.

Ethyl atropate is an important intermediate for preparing pharmaceutical active ingredients such as bicyclophenamine, bornaprine and tilidine. The opioid analgesic tilidine can be prepared, for example, by reacting ethyl atropate with dimethylaminobutadiene. It is important for this synthesis that the ethyl atropate used as starting material has a minimal content of methyl atropate because such an impurity results in tilidine being contaminated with the corresponding methyl ester, which can be removed only at disproportionately great expense. It is therefore necessary for a practicable synthesis of tilidine to use as starting material an ethyl atropate whose content of methyl ester does not exceed 0.05%.

Ethyl atropate with a methyl atropate content not exceeding 0.05% can be obtained in a relatively complicated, two-stage process (Helv. Chim. Acta 30, 1349 (1947)) as long as the starting materials do not contain more than 0.05% of methyl compounds. This process involves ethyl phenylacetate being condensed with diethyl oxalate in the presence of sodium ethanolate to give diethyl 2-oxo-3-phenylsuccinate, Na salt. Subsequent reaction with formaldehyde in the presence of potassium carbonate results in ethyl atropate with a methyl ester content not exceeding 0.05%.

DE 33 17 356 describes a one-stage process in which ethyl phenylacetate is reacted with paraformaldehyde in the presence of potassium carbonate in a solid/liquid phase transfer-catalyzed reaction to give ethyl atropate. However, in this case, even on use of ethyl phenylacetate with a methyl ester content of 0.1% there is formation of unacceptably large amounts of methyl atropate, probably as a result of the formation of methanol by a Cannizzaro reaction of formaldehyde. Thus, on use of toluene as solvent, about 2% of the methyl ester are obtained.

EP-A 3 670 describes a one-stage process for preparing 2-arylacrylic esters, in which arylacetic esters are reacted with formaldehyde in a polar solvent in the presence of a base to give 2-arylacrylic esters. However, reaction of ethyl phenylacetate with paraformaldehyde by the general method results in a reaction mixture which comprises only about 25% ethyl atropate.

We have now found a practicable and simple process for preparing ethyl atropate with a methyl ester content not exceeding 0.05%.

The invention relates to a process for preparing ethyl atropate with a methyl ester content not exceeding 0.05% by reacting ethyl phenylacetate with paraformaldehyde in the presence of a base, wherein the product employed as ethyl phenylacetate contains not more than 0.03% of the corresponding methyl phenylacetate, and wherein the reaction is carried out in N-methylpyrrolidone or N,N-dimethylformamide.

In the process, 1 mol of ethyl phenylacetate is reacted with 1 to 2, preferably 1.4 to 1.6, equivalents of paraformaldehyde.

The base usually employed is potassium carbonate, which is used in an amount of from 1 to 2, preferably from 1.4 to 1.8 mol per mole of ethyl phenylacetate.

The reaction is carried out at 70 to 90° C. It is usually complete after 1.5 to 3 h.

The process according to the invention affords ethyl atropate in yields exceeding 50% with high product purity (more than 90% (GC)). The methyl ester content in the ethyl atropate prepared by the novel process is in the range from 0.02 to 0.05%.

In contrast to the two-stage process of Helv. Chim. Acta 30, 1349 (1947), there is no isolation and storage of an intermediate in the novel process. The novel process can moreover be carried out in a considerably shorter time. Finally, the novel process does not require sodium methoxide, which can be stored for only a limited time and is corrosive.

EXAMPLE 94 g of ethyl phenylacetate (methyl ester content 0.01%) were stirred in 300 ml of N-methylpyrrolidone with 120 g of potassium carbonate and 25 g of paraformaldehyde at 75 to 80° C. for 1.5 h. After cooling, 150 ml of water were added, and the aqueous phase was separated off. The N-methylpyrrolidone phase was extracted twice with 75 ml of diisopropyl ether each time. The combined diisopropyl ether phases were washed with 50 ml of water and concentrated in vacuo. 58 g of product were obtained, corresponding to 54 g of ethyl atropate (53% of theory) with a methyl atropate content of 0.03%.

We claim:

1. A process for the production of ethyl atropate containing less than 0.05% of methyl atropate in a single stage process, which process comprises reacting ethyl phenylacetate with paraformaldehyde in the presence of a base, wherein the ethyl phenylacetate contains not more than 0.03% of methyl phenylacetate wherein the reaction is carried out in the presence of N-methylpyrrolidone or N,N-dimethylformamide, and potassium carbonate at 75 to 80° C. for 1.5 hours, and wherein the yield of ethyl atropate is greater than 50%.

* * * * *